(12) United States Patent
Sim et al.

(10) Patent No.: US 10,130,631 B2
(45) Date of Patent: Nov. 20, 2018

(54) CML THERAPEUTIC AGENTS WITH REDUCED DRUG-RESISTANCE AND SIDE-EFFECT COMPRISING 1,6-DISUBSTITUTED INDOLE COMPOUNDS

(71) Applicant: KOREA INSTITUTE OF SCIENCE AND TECHNOLOGY, Seoul (KR)

(72) Inventors: Tae Bo Sim, Seoul (KR); Ho Jong Yoon, Seoul (KR); Woo Young Hur, Seoul (KR); Yun Ju Nam, Seoul (KR); Hwan Geun Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 12 days.

(21) Appl. No.: 15/677,742

(22) Filed: Aug. 15, 2017

(65) Prior Publication Data

US 2018/0050036 A1 Feb. 22, 2018

(30) Foreign Application Priority Data

Aug. 16, 2016 (KR) .................. 10-2016-0103814

(51) Int. Cl.
*A61K 31/506* (2006.01)
*A61K 31/519* (2006.01)
*A61K 31/5377* (2006.01)

(52) U.S. Cl.
CPC .......... *A61K 31/506* (2013.01); *A61K 31/519* (2013.01); *A61K 31/5377* (2013.01)

(58) Field of Classification Search
None
See application file for complete search history.

(56) References Cited

U.S. PATENT DOCUMENTS 8,765,749 B2 * 7/2014 Sim ............... C07D 403/04
514/235.8
2012/0271048 A1 10/2012 Sim et al.

FOREIGN PATENT DOCUMENTS

KR 10-1116756 B1 3/2012
WO WO 2011/052923 A2 5/2011

OTHER PUBLICATIONS

"FDA halts then allows sales of Ariad's leukemia medication", Nat. Biotech., Jan. 2014, vol. 32, No. 1, pp. 9-11.
Cortes et al., "Ponatinib in Refractory Philadelphia Chromosome-Positive Leukemias" N. Engl. J. Med., 2012, vol. 367, No. 22, pp. 2075-2088.
Mayer et al., "Fatal progressive cerebral ischemia in CML under third-line treatment with ponatinib", Leukemia, 2014, vol. 28, pp. 976-977.
Mian et al., "PF-114, a potent and selective inhibitor of native and mutated BCR/ABL is active against Philadelphia chromosome-positive (Ph+) leukemias harboring the T315I mutation", Leukemia, 2015, vol. 29, pp. 1104-1114.

* cited by examiner

*Primary Examiner* — Kortney L. Klinkel
*Assistant Examiner* — Tori Strong
(74) *Attorney, Agent, or Firm* — Birch, Stewart, Kolasch & Birch, LLP

(57) ABSTRACT

The present invention relates to a therapeutic agent for chronic myelogenous leukemia with reduced drug-resistance and side-effects containing a 1,6-disubstituted indole compound.

4 Claims, 2 Drawing Sheets

CML THERAPEUTIC AGENTS WITH REDUCED DRUG-RESISTANCE AND SIDE-EFFECT COMPRISING 1,6-DISUBSTITUTED INDOLE COMPOUNDS

CROSS-REFERENCE TO RELATED APPLICATION

This application claims under 35 U.S.C. § 119(a) the benefit of Korean Patent Application No. 10-2016-0103814 filed on Aug. 16, 2016, the entire contents of which are incorporated herein by reference.

BACKGROUND (a) Technical Field

The present disclosure relates to CML therapeutic agents with reduced drug-resistance and side-effect comprising 1,6-disubstituted indole compounds.

(b) Background Art

Chronic myelogenous leukemia (CML) is a type of hematologic malignancy caused by abnormally enlarged clones of hematopoietic stem cells with the Philadelphia chromosome. The Philadelphia chromosome results in the formation and continued activity of the Bcr-Abl fusion protein, which is the causative protein of CML. These abnormal Bcr-Abl proteins are expressed in more than 90% of patients with chronic myelogenous leukemia (CML) and about 40% of patients with acute lymphoblastic leukemia (ALL), and the sustained activity of Bcr-Abl further promotes leukemia. For this reason, Bcr-Abl tyrosine kinase has been regarded as a promising drug target for CML.

Imatinib as a therapeutic agent for chronic myelogenous leukemia has been commercialized and marketed as Gleevec, but a variety of point mutant species having Gleevec resistance have been reported recently. In particular, T315I, known as a gatekeeper mutant species, is not treated with Gleevec, nor with Nilotinib, Dasatinib, or Bosutinib, which are known as second-generation Bcr-Abl inhibitors. Although many studies have been conducted to overcome these gatekeeper mutant species, only Ponatinib has been reported to be the only drug approved for limited clinical use thus far.

Ponatinib has been reported to strongly inhibit wild-type Bcr-Abl and T315I-Bcr-Abl in vitro and in vivo, and has been exhibited to have excellent efficacy in phase 1 clinical trial (NCT00660920) and phase 2 clinical trial (NCT01207440) with patients with chronic myelogenous leukemia having T315I. However, it has been reported that Ponatinib may cause side-effects such as myelosuppression and pancreatitis due to low selectivity of kinase by simultaneously activating various kinases such as VEGFR2, PDGFR, KIT, FLT3, and FGFR (see Non-Patent Document 1). In addition, in the recent phase 3 clinical trial (NCT01650805), side-effects such as rapid cardiovascular disease caused by the strong VEGFR2 inhibitory effect of Ponatinib were observed and clinical trials and sales were discontinued (see Non-Patent Document 2). Therefore, it is urgently required to develop a therapeutic agent for CML which inhibits the activity of T315I-Bcr-Abl gatekeeper mutation, at the same time, has excellent selectivity for kinase, and in particular, does not have inhibitory activity for VEGFR2.

Meanwhile, the present inventors have synthesized 1,6-substituted novel indole compounds in Korean Patent Registration Publication No. 10-1116756 (Patent Document 1), and found that these compounds having inhibitory activity for B-Raf kinase and human melanoma cell lines (A375P, SK-MEL28), discloses that they are useful as a preventive and therapeutic agent for tumor diseases.

PRIOR ART DOCUMENTS

Patent Document (Patent Document 1) Korean Patent Registration Publication No. 10-1116756 entitled "NOVEL 1,6-SUBSTITUTED INDOLE COMPOUND HAVING AN ACTIVITY OF SUPPRESSING PROTEIN KINASE"

Non-Patent Documents (Non-Patent Document 1) "Ponatinib in Refractory Philadelphia Chromosome-Positive Leukemias". N. Engl. J. Med. 367, 2075-2088 (2012)

(Non-Patent Document 2) FDA halts then allows sales of Ariad's leukemia medication. Nat. Biotech. 32, 9-11 (2014)

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

The present inventors have continuously studied to develop a compound effective for the target treatment, prevention and alleviation of chronic myelogenous leukemia (CML) which may be fatal in tumor diseases. As a result, compounds which inhibit the proliferation of Bcr-Abl, a causative gene of chronic myelogenous leukemia (CML), has excellent inhibitory activity against T315I-Bcr-Abl gatekeeper mutant species, and has poor inhibitory activity against VEGFR2 were selected. In addition, they confirmed through in vivo experiments that the compound thus selected does not exhibit drug toxicity, and completed the present invention.

Accordingly, the present invention aims at providing a pharmaceutical composition which is useful for the treatment, prevention and alleviation of chronic myelogenous leukemia, which has excellent inhibitory activity against Bcr-Abl, which is a causative gene of chronic myelogenous leukemia and its point mutant species, and reduces drug-resistance and side-effects simultaneously because no inhibitory activity is exhibited in VEGFR2 kinase.

In order to solve the above-mentioned problems, the present invention provides a pharmaceutical composition for the treatment, prevention and alleviation of chronic myelogenous leukemia with reduced drug side-effects, which comprises a 1,6-disubstituted indole compound represented by the following formula 1 or a pharmaceutically acceptable salt thereof as an active ingredient.

[Formula 1]

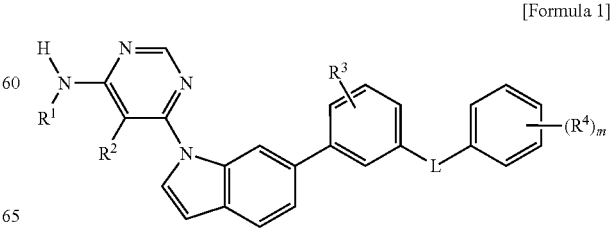

In Formula 1,

L is selected from —NR⁵C(O)— or —NR⁵C(O)NR⁶—, $R^1$ and $R^2$ are each a hydrogen atom, or $R^1$ and $R^2$ may bond to each other to form a pentagonal ring, $R^3$ is selected from a hydrogen atom or a $C_1$-$C_6$ alkyl group, $R^4$ is selected from the group consisting of $C_1$-$C_6$ haloalkyl, $C_1$-$C_6$ alkoxy,

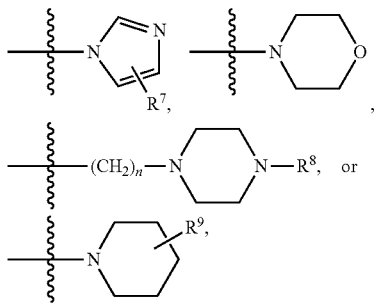

$R^5$, $R^6$, $R^7$ and $R^8$ are each selected from a hydrogen atom or a $C_1$-$C_6$ alkyl group, $R^9$ is selected from a hydrogen atom or a hydroxyl group, m is the number of the substituent $R^4$ and is an integer of 1 to 3, and n is an integer of 0 to 3.

The pharmaceutical composition of the present invention has a proliferation inhibitory activity against a Bcr-Abl fusion protein which is a causative gene of chronic myelogenous leukemia (CML), and has inhibitory activity against T315I-Bcr-Abl gatekeeper mutant species, and does not have activity against VEGFR2 protein kinase. Accordingly, the pharmaceutical composition of the present invention has an inhibitory activity against Bcr-Abl fusion protein, thereby having an effect of treating, preventing or alleviating chronic myelogenous leukemia (CML). In addition, the pharmaceutical composition of the present invention has an inhibitory activity against a T315I-Bcr-Abl gatekeeper mutant species, thereby having an effect of overcoming resistance of a drug. In addition, since the pharmaceutical composition of the present invention does not have activity against VEGFR2 protein kinase, it has an effect of overcoming side-effects of drugs such as cardiovascular disease development exhibited to patients taking T315I inhibiting drugs.

Accordingly, the pharmaceutical composition of the present invention is useful as a target therapeutic agent capable of treating chronic myelogenous leukemia (CML) while greatly reducing drug-resistance and side-effects.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein.

Figure 1:
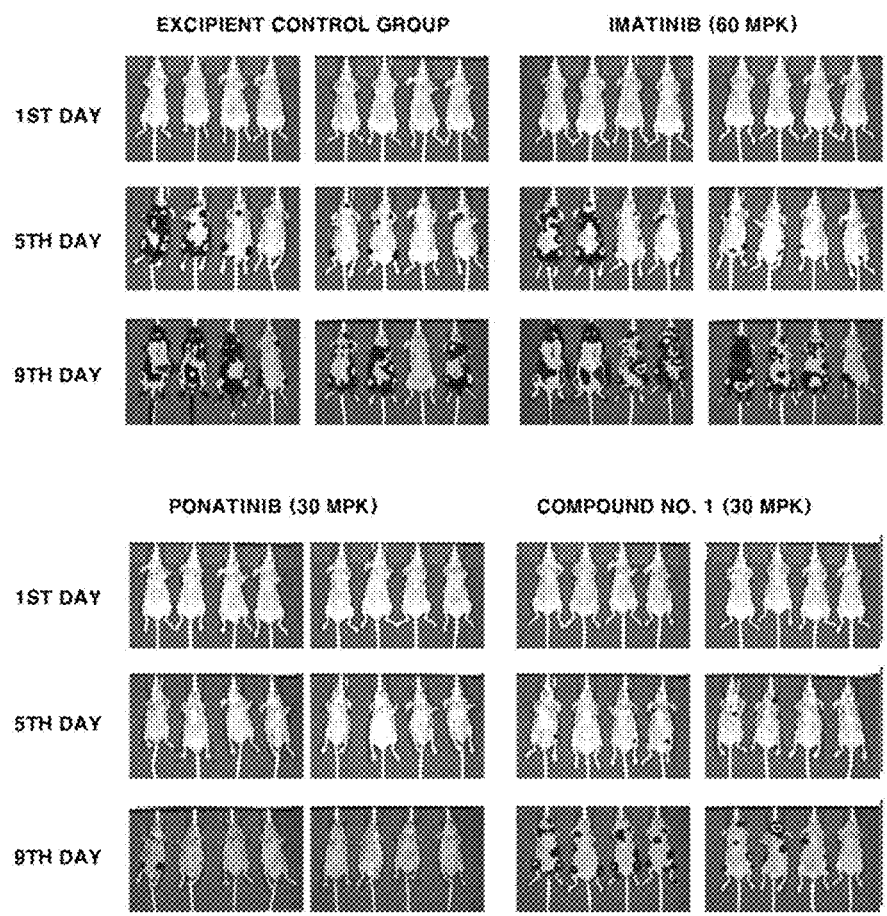
FIG. 1 is a photograph of the bioluminescence measured on the $1^{st}$, $5^{th}$ and $9^{th}$ days from the oral administration of each of the excipient control group, Imatinib, Ponatinib or a compound of Compound No. 1, respectively.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a pharmaceutical composition for the treatment, prevention and alleviation of chronic myelogenous leukemia with reduced drug-resistance and side-effects comprising 1,6-disubstituted indole compounds represented by the following formula 1 or a pharmaceutically acceptable salt thereof as an active ingredient.

[Formula 1]

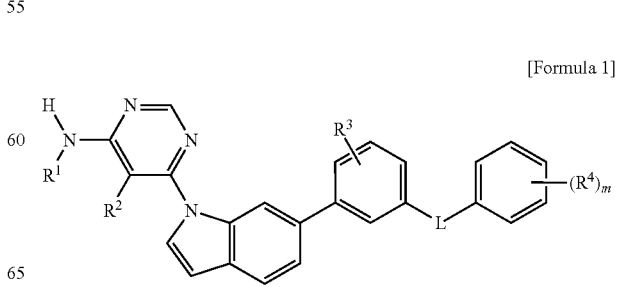

In Formula 1,

L is selected from —NR$^5$C(O)— or —NR$^5$C(O)NR$^6$—,

R$^1$ and R$^2$ are each a hydrogen atom, or R$^1$ and R$^2$ may bond to each other to form a pentagonal ring, R$^3$ is selected from a hydrogen atom or a C$_1$-C$_6$ alkyl group, R$^4$ is selected from the group consisting of C$_1$-C$_6$ haloalkyl, C$_1$-C$_6$ alkoxy,

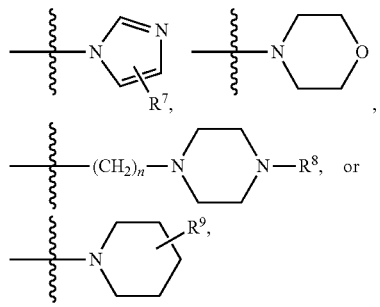

R$^5$, R$^6$, R$^7$ and R$^8$ are each selected from a hydrogen atom or a C$_1$-C$_6$ alkyl group, R$^9$ is selected from a hydrogen atom or a hydroxyl group, m is the number of the substituent R$^4$ and is an integer of 1 to 3, and n is an integer of 0 to 3.

In the compound represented by the formula (1) included in the pharmaceutical composition according to the present invention, preferably, it is a compound wherein said L is —NHC(O)—; said R$^1$ and R$^2$ are each a hydrogen atom, or R$^1$ and R$^2$ are bonded to each other to form a pyrrolo[2,3-d]pyrimidine ring; said R$^3$ is a methyl group; said R$^4$ is a trifluoromethyl group, a 4-methyl-1H-imidazole-1-yl group, a morpholino group, a 4-methyl-piperazine-1-yl group, a (4-methyl-piperazine-1-yl)methyl group or a 4-hydroxypiperidine-1-yl group; and said m is an integer of 2.

Specific examples of the compound represented by formula 1 included in the pharmaceutical composition according to the present invention are provided as follows:

N-(3-(1-(6-aminopyridine-4-yl)-1H-indole-6-yl)-4-methylphenyl)-3-(4-methyl-1 H-imidazole-1-yl)-5-(trifluoromethyl)benzamide (Compound No. 1);

N-(3-(1-(6-aminopyridine-4-yl)-1H-indole-6-yl)-4-methylphenyl)-3-(4-hydroxypiperidine-1-yl)-5-(trifluoromethyl)benzamide (Compound No. 2);

N-(3-(1-(6-aminopyridine-4-yl)-1H-indole-6-yl)-4-methylphenyl)-3-morpholino-5-(trifluoromethyl)benzamide (Compound No. 3);

N-(3-(1-(6-aminopyridine-4-yl)-1H-indole-6-yl)-4-methylphenyl)-3-(4-methylpiperazine-1-yl)-5-(trifluoromethyl)benzamide (Compound No. 4);

N-(3-(1-(6-aminopyridine-4-yl)-1H-indole-6-yl)-4-methylphenyl)-4-(4-methylpiperazine-1-yl)-5-(trifluoromethyl)benzamide (Compound No. 5);

N-(3-(1-(6-aminopyridine-4-yl)-1H-indole-6-yl)-4-methylphenyl)-3-((4-methylpiperazine-1-yl)methyl)-5-(trifluoromethyl)benzamide (Compound No. 6);

N-(3-(1-(6-aminopyrimidine-4-yl)-1H-indole-6-yl)phenyl)-3-(4-methyl-1H-imidazole-1-yl)-5-(trifluoromethyl)benzamide (Compound No. 7);

N-(3-(1-(6-aminopyrimidine-4-yl)-1H-indole-6-yl)phenyl)-3-morpholino-5-(trifluoromethyl)benzamide (Compound No. 8);

1-(3-(1-(6-aminopyrimidine-4-yl)-1H-indole-6-yl)-4-methylphenyl)-3-(2-methoxyphenyl) urea (Compound No. 9);

1-(3-(1-(7H-pyrrolo[2,3-d]pyrimidine-4-yl)-1H-indole-6-yl)phenyl)-3-(2-methoxyphenyl)urea (Compound No. 10);

N-(3-(1-(7H-pyrrolo[2,3-d]pyrimidine-4-yl)-1H-indole-6-yl)-4-methylphenyl)-3-(4-methyl-1H)-imidazole-1-yl)-5-(trifluoromethyl)benzamide (Compound No. 11);

N-(3-(1-(7H-pyrrolo[2,3-d]pyrimidine-4-yl)-1H-indole-6-yl)-4-methylphenyl)-3-(4-hydroxypiperidine-1-yl)-5-(trifluoromethyl)benzamide (Compound No. 12);

N-(3-(1-(7H-pyrrolo[2,3-d]pyrimidine-4-yl)-1H-indole-6-yl)-4-methylphenyl)-3-morpholino-5-(trifluoromethyl)benzamide (Compound No. 13);

N-(3-(1-(7H-pyrrolo[2,3-d]pyrimidine-4-yl)-1H-indole-6-yl)-4-methylphenyl)-3-(4-methylpiperazine-1-yl)-5-(trifluoromethyl)benzamide (Compound No. 14);

N-(3-(1-(7H-pyrrolo[2,3-d]pyrimidine-4-yl)-1H-indole-6-yl)-4-methylphenyl)-4-(4-methylpiperazine-1-yl)-5-(trifluoromethyl)benzamide (Compound No. 15); or N-(3-(1-(7H-pyrrolo[2,3-d]pyrimidine-4-yl)-1H-indole-6-yl)-4-methylphenyl)-4-((4-methylpiperazine-1-yl)methyl)-3-(trifluoromethyl)benzamide (Compound No. 16).

The 1,6-disubstituted indole compound represented by formula 1 is a compound disclosed in Patent Document 1 (Korean Patent Registration Publication No. 10-1116756) or a derivative thereof. Therefore, the compound represented by formula 1 included in the pharmaceutical composition of the present invention can be easily synthesized and used by applying the method disclosed in Patent Document 1 or the method disclosed in the book related to organic synthesis.

The compound represented by the formula 1 included in the pharmaceutical composition according to the present invention may be included in the form of a pharmaceutically acceptable salt. Such pharmaceutically acceptable salt can be prepared by the conventional methods in the pertinent technical field. For example, pharmaceutically acceptable salts of these acids can be formed together with non-toxic inorganic acids such as hydrochloric acid, bromic acid, sulfonic acid, amidosulfuric acid, phosphoric acid and nitric acid or non-toxic organic acids such as propionic acid, succinic acid, glycolic acid, stearic acid, lactic acid, tartaric acid, citric acid, paratoluenesulfonic acid, and methanesulfonic acid, can form.

The compound represented by the formula 1 has excellent proliferation inhibitory activity against Bcr-Abl fusion protein, which is a causative gene of chronic myelogenous leukemia (CML). In addition, the compound represented by the formula 1 has excellent inhibitory activity against a T315I-Bcr-Abl gatekeeper mutant species. In addition, the compound represented by the formula 1 does not exhibit inhibitory activity against VEGFR2 protein kinase.

Accordingly, the pharmaceutical composition containing the compound represented by the formula 1, a pharmaceutically acceptable salt thereof, a solvate thereof, and a hydrate thereof as an active ingredient is useful as a drug-resistant chronic myelogenous leukemia (CML) therapeutic agent. In particular, the pharmaceutical composition of the present invention has selectivity that exhibits inhibitory activity against various protein kinases such as Raf kinase and does not exhibit inhibitory activity against VEGFR2 protein kinase. Therefore, it is useful as a therapeutic agent of chronic myelogenous leukemia (CML) while reducing side-effects such as cardiovascular disease.

The pharmaceutical composition of the present invention contains the compound represented by the formula 1 or a pharmaceutically acceptable salt thereof, a solvate thereof, and a hydrate thereof as an active ingredient, wherein a conventional non-toxic pharmaceutically acceptable carrier, an adjuvant and an excipient are added to be prepared into an ordinary preparation in the pharmaceutical field, for example, oral administration such as tablets, capsules, troches, solutions, and suspensions, or parenteral administration.

Examples of excipients that can be used in the pharmaceutical composition of the present invention include sweeteners, binders, solubilizers, solubilizer adjuvants, wetting agents, emulsifiers, isotonizing agents, adsorbents, disintegrants, antioxidants, preservatives, lubricants, fillers, perfumes, and the like. For example, examples are lactose, dextrose, sucrose, mannitol, sorbitol, cellulose, glycine, silica, talc, stearic acid, stearin, magnesium stearate, magnesium aluminum silicate, starch, gelatin, tragacanth gum, arginine acid, sodium alginate, methylcellulose, sodium carboxymethylcellulose, agar, Water, ethanol, polyethylene glycol, polyvinylpyrrolidone, sodium chloride, calcium chloride, orange essence, strawberry essence, vanilla flavor, and the like.

The dose of the compound according to the present invention to the human body may vary depending on the age, body weight, gender, dosage form, health condition, and disease severity of a patient. Based on an adult patient weighing 70 kg, it is generally 0.01 to 1,000 mg/day. Depending on the judgment of a doctor or a pharmacist, it may be administered once or several times a day at a predetermined time interval.

As discussed above, the present invention will be described in more detail with reference to the following examples, preparation examples and test examples. However, the following examples, preparation examples and test examples are merely illustrative of the present invention, but the scope of the present invention is not limited thereto.

EXAMPLES

Compound Nos. 1 to 8 were synthesized based on the following reaction formula 1.

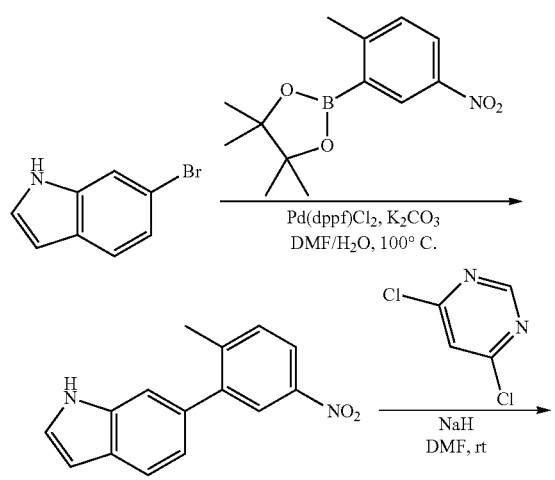

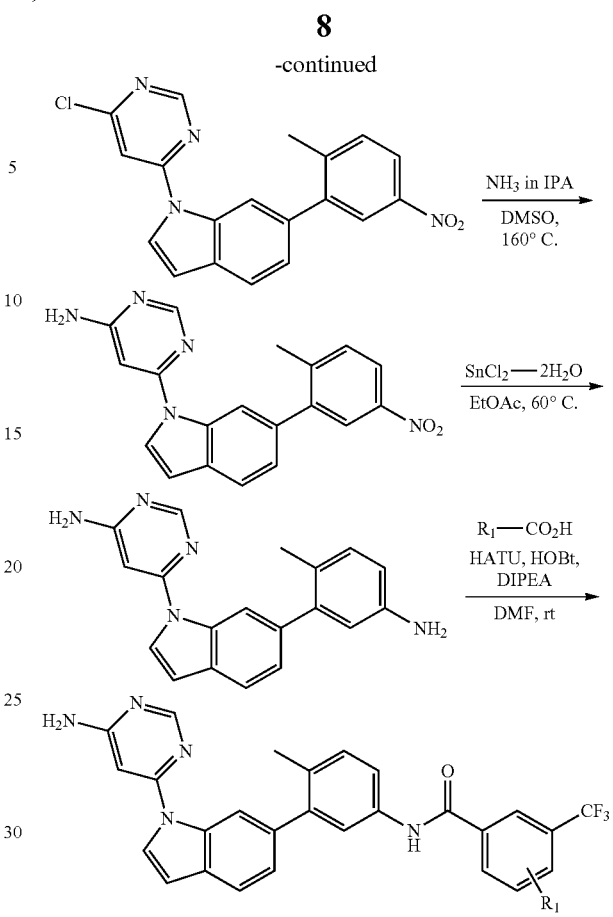

Example 1

N-(3-(1-(6-aminopyridine-4-yl)-1H-indole-6-yl)-4-methylphenyl)-3-(4-methyl-1H-imidazole-1-yl)-5-(trifluoromethyl)benzamide (Compound No. 1)

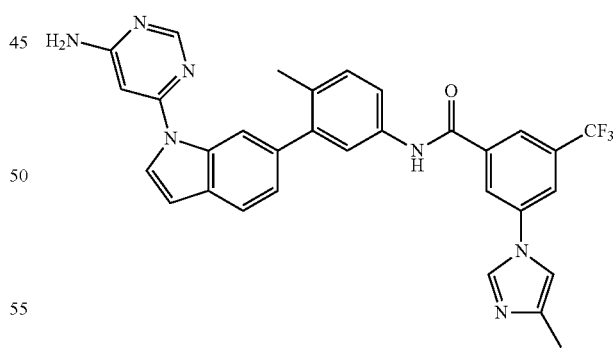

Step 1: 6-(2-methyl-5-nitrophenyl)-1H-indole 6-bromoindole (2.64 g, 13.5 mmol), 4,4,5,5-tetramethyl-2-(2-methyl-5-nitrophenyl)-1,3,2-dioxaboroline (4.1 g, 14.8 mmol) and potassium carbonate (3.9 g, 27 mmol) were added to the mixture solution of DMF/water (4:1, 27 mL), and nitrogen gas was injected for 5 minutes to remove the gas included in the mixture solution. Then, the reaction vessel was placed in an oil bath heated to 100° C., and Pd(dppf)Cl$_2$ (1.1 g, 1.35 mmol) was added thereto, followed by stirring for 30 minutes. After the reaction was completed, the mixture solution was filtered using a celite pad. The filtrate was extracted with ethyl acetate and water. The collected organic layers were dried over anhydrous sodium sulfate and concentrated. The residue was purified by MPLC to obtain the target compound (3.53 g, 72%) as a yellow solid.

$^1$H NMR (400 MHz, CDCl$_3$) δ 8.27 (bs, 1H), 8.18 (d, J=2.8 Hz, 1H), 8.10 (dd, J=2.4 Hz, 8.4 Hz, 1H), 7.71 (d, J=4 Hz, 1H), 7.42 (d, J=4.2 Hz, 1H), 7.34 (s, 3H), 7.30 (t, J=2.8 Hz, 1 H), 7.07 (dd, J=1.6 Hz, 1H), 6.64-6.62 (m, 1H), 2.40 (s, 3H)

Step 2: 1-(6-chloropyrimidine-4-yl)-6-(2-methyl-5-nitrophenyl)-1H-indole 6-(2-methyl-5-nitrophenyl)-1H-indole (1.61 g, 6.38 mmol) and 4,6-dichloropyrimidine (1 g, 6.7 mmol) were dissolved in DMF (13 mL), sodium hydride (60% mineral oil dispersion, 0.51 g, 12.8 mmol) was slowly added and stirred. After the reaction was completed, the mixture solution was added to ice water and stirred for 1 hour, followed by filtration and drying to obtain the target compound (2.28 g, 98%) as an ivory solid.

$^1$H NMR (400 MHz, CDCl$_3$) δ 8.86 (s, 3H), 8.61 (s, 3H), 8.19 (s, 3H), 8.13 (dd, J=2 Hz, 8.4 Hz, 1H), 7.71-7.69 (m, 2H), 7.45 (d, J=8.4 Hz, 1H), 7.40 (s, 3H), 7.26-7.22 (m, 1H), 6.86 (d, J=3.6 Hz, 1H), 2.41 (s, 3H)

Step 3: 6-(6-(2-methyl-5-nitrophenyl)-1H-indole-1-yl)pyrimidine-4-amine

In an airtight container, 1-(6-chloropyrimidine-4-yl)-6-(2-methyl-5-nitrophenyl)-1H-indole (2 g, 5.48 mmol) was dissolved in DMSO (27.4 mL). After adding an ammonia solution (2 M, 27.4 mL, 54.8 mmol) dissolved in isopropanol, it was heated to 160° C. and stirred for 2 hours. The reaction solution was cooled to room temperature and extracted with ethyl acetate and water. The collected organic layers were dried over anhydrous sodium sulfate and concentrated. The residue was purified by MPLC to obtain the target compound (2.31 g, 82%) as a yellow solid.

$^1$H NMR (400 MHz, CDCl$_3$) δ 8.35 (s, 1H), 8.13 (dd, J=2.4 Hz, 8,4 Hz 1H), 8.03 (d, J=2.4 Hz, 1H), 7.99 (d, J=3.6 Hz, 1H), 7.72 (d, J=8 Hz, 1H), 7.60 (d, J=8.4 Hz, 1H), 7.20 (dd, J=1.2 Hz, 8.4 Hz, 1H), 7.20 (dd, J=1.2 Hz, 8.4 Hz, 1H), 7.01 (s, 2H), 6.82 (d, J=3.6, 1H), 6.64 (s, 1H), 2.35 (s, 3H)

Step 4: 6-(6-(5-amino-2-methylphenyl)-1H-indole-1-yl)pyrimidine-4-amine 6-(6-(2-methyl-5-nitrophenyl)-1H-indole-1-yl)pyrimidine-4-amine (1 g, 2.8 mmol) was dissolved in ethanol (14 mL), tin chloride hydrate (SnCl$_2$.2H$_2$O, 3.16 g, 14 mmol) was added thereto, followed by stirring at 80° C. for 1 hour. After the reaction was completed, the reaction solution was diluted with methylene chloride, and neutralized by adding potassium carbonate at 0° C. The organic layers were then extracted with water and methylene chloride, and the collected organic layers were dried over anhydrous sodium sulfate and concentrated. The residue was purified by MPLC to obtain the target compound (776 mg, 88%).

Step 5: N-(3-(1-(6-aminopyridine-4-yl)-1H-indole-6-yl)-4-methylphenyl)-3-(4-methyl-1H-imidazole-1-yl)-5-(trifluoromethyl)benzamide 6-(6-(5-amino-2-methylphenyl)-1H-indole-1-yl)pyrimidine-4-amine (800 mg, 2.55 mmol) and 3-(4-methyl-1H-imidazole-1-yl)-5-(trifluoromethyl)benzoic acid (816 mg, 3.18 mmol) were dissolved in DMF (10 mL). After 1-ethyl-3-(3-dimethylaminopropyl) carbodiimide (EDCl, 860 mg, 4.5 mmol), 1-hydroxybenzotriazole (HOBt; 860 mg, 4.5 mmol), diisopropylethylamine (1.6 mL, 9 mmol) were added to the reaction solution, they were stirred at room temperature for 6 hours. After the reaction was completed, it was extracted with ethyl acetate and water. The collected organic layers were dried over anhydrous sodium sulfate and concentrated. The residue was washed with acetone and ether to obtain the target compound (1.1 g, 76%).

$^1$H NMR (400 MHz, DMSO-d$_6$) δ 10.49 (s, 1H), 8.45 (s, 1H), 8.39 (d, J=1.6 Hz, 1H), 8.37 (d, J=1.2 Hz, 1H), 8.34 (s, 1H), 8.22 (s, 1H), 8.18 (s, 1H), 7.97 (d, J=3.6 Hz, 1H), 7.77 (dd, J=2.4 Hz, 8.4 Hz, 1H), 7.70 (d, J=8.4 Hz, 1H), 7.67 (dd, J=2.0 Hz, 11.2 Hz, 1H), 7.33 (d, J=8.4 Hz, 1H), 7.18 (dd, J=1.2 Hz, 8.0 Hz, 1H), 7.03 (s, 2H), 6.81 (dd, J=0.4 Hz, 3.6 Hz, 1H), 6.65 (d, J=0.8 Hz, 1H), 2.24 (s, 3H), 2.17 (d, J=0.8 Hz, 3H)

Example 2

N-(3-(1-(6-aminopyridine-4-yl)-1H-indole-6-yl)-4-methylphenyl)-3-(4-hydroxypiperidine-1-yl)-5-(trifluoromethyl)benzamide (Compound No. 2)

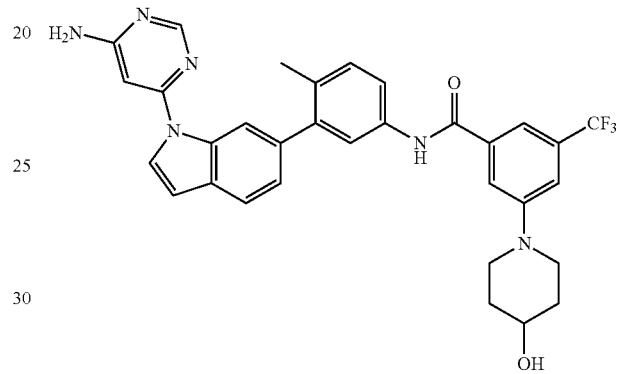

The target compound was obtained using the method described in Example 1 above and an appropriate starting material.

$^1$H NMR (400 MHz, DMSO-d$_6$) δ 10.31 (s, 1H), 8.35 (s, 1H), 8.30 (s, 1H), 7.96 (d, J=3.6 Hz, 1H), 7.74 (dd, J=2.0 Hz, 8.0 Hz, 1H), 7.70-7.68 (m, 2H), 7.62 (d, J=2.0 Hz. 1H), 7.56 (s, 1H), 7.32 (s, 1H), 7.30 (d, J=8.4 Hz, 1H), 7.17 (dd, J=1.6 Hz, 8.0 Hz, 1H), 7.01 (bs, 2H), 6.80 (d, J=3.6 Hz, 1H), 6.63 (d, J=0.4 Hz, 1H), 4.71 (d, J=4.0 Hz, 1H), 3.70-3.66 (m, 3H), 3.04-2.98 (m, 2H), 2.22 (s, 2H), 1.83-1.81 (m, 2H), 1.49-1.42 (m, 2H)

Example 3

N-(3-(1-(6-aminopyridine-4-yl)-1H-indole-6-yl)-4-methylphenyl)-3-morpholino-5-(trifluoromethyl)benzamide (Compound No. 3)

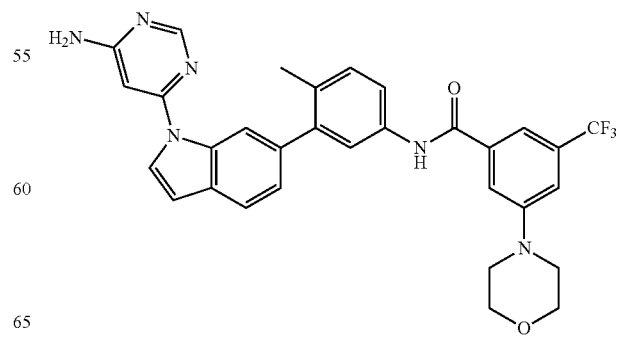

The target compound was obtained using the method described in Example 1 above and an appropriate starting material.

¹H NMR (400 MHz, CDCl₃-d₆) δ 8.76 (s, 1H), 8.39 (s, 1H), 8.06 (s, 1H), 7.69 (d, J=2.8 Hz, 1H), 7.53 (d, J=8.0 Hz, 1H), 7.47-7.40 (m, 4H), 7.11 (s, 1H), 7.02 (dd, J=8.0 Hz, 17.2 Hz, 1H), 6.62 (d, J=3.2 Hz, 1H), 6.47 (s, 1H), 5.71 (bs, 2H), 3.75 (s, 4H), 3.11 (s, 4H), 2.13 (s, 3H)

Example 4

N-(3-(1-(6-aminopyridine-4-yl)-1H-indole-6-yl)-4-methylphenyl)-3-(4-methylpiperazine-1-yl)-5-(trifluoromethyl)benzamide (Compound No. 4)

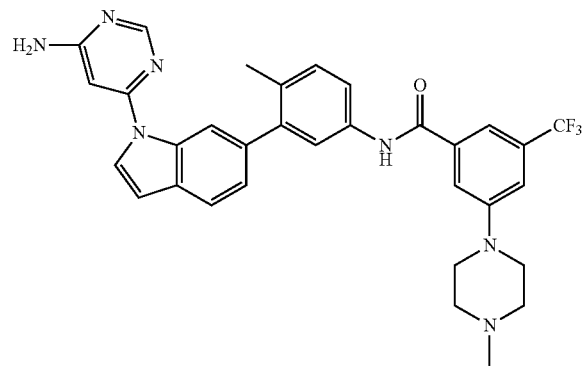 [SMILES: Cc1ccc(NC(=O)c2cc(N3CCN(C)CC3)cc(C(F)(F)F)c2)cc1-c1ccc2ccn(-c3cc(N)ncn3)c2c1]

The target compound was obtained using the method described in Example 1 above and an appropriate starting material.

¹H NMR (400 MHz, CDCl₃-d₆) δ 8.91 (bs, 1H), 8.44 (s, 1H), 8.16 (s, 1H), 7.85 (d, J=3.6 Hz, 1H), 7.82 (d, J=8.4 Hz, 1H), 7.75 (s, 1H), 7.69-7.62 (m, 3H), 7.23 (d, J=8.4 Hz, 1H), 7.13 (s, 1H), 6.82 (s, 1H), 6.71 (d, J=3.2 Hz, 1H), 5.80 (bs, 2H), 3.60 (bs, 4H), 3.07 (bs, 4H), 2.61 (s, 3H), 2.31 (s, 3H)

Example 5

N-(3-(1-(6-aminopyridine-4-yl)-1H-indole-6-yl)-4-methylphenyl)-4-(4-methylpiperazine-1-yl)-5-(trifluoromethyl)benzamide (Compound No. 5)

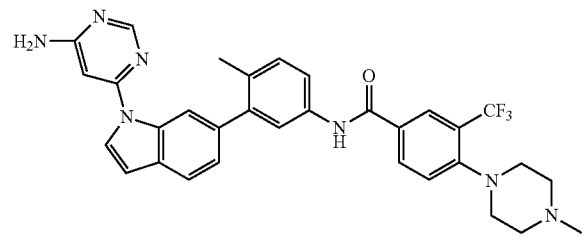 [SMILES: Cc1ccc(NC(=O)c2ccc(N3CCN(C)CC3)c(C(F)(F)F)c2)cc1-c1ccc2ccn(-c3cc(N)ncn3)c2c1]

The target compound was obtained using the method described in Example 1 above and an appropriate starting material.

¹H NMR (400 MHz, DMSO-d₆) δ 10.34 (s, 1H), 8.38 (s, 1H), 8.33 (s, 1H), 8.25 (s, 1H), 8.24 (dd, J=2.0 Hz, 8.4 Hz, 1H), 7.99 (d, J=3.6 Hz, 1H), 7.77 (dd, J=2.0 Hz, 8.0 Hz, 1H), 7.71 (d, J=8.0 Hz, 1H), 7.66 (d, J=2.0 Hz, 1H), 7.60 (d, J=8.4 Hz, 1H), 7.31 (d, J=8.4 Hz, 1H), 7.19 (dd, J=1.2 Hz, 8.0 Hz, 2H), 7.04 (bs, 2H), 6.83 (d, J=3.2 Hz, 1H), 6.66 (s, 1H), 2.98-2.96 (m, 4H), 2.52-2.51 (m, 4H), 2.25 (s, 3H), 2.24 (s, 3H)

Example 6

N-(3-(1-(6-aminopyridine-4-yl)-1H-indole-6-yl)-4-methylphenyl)-3-((4-methylpiperazine-1-yl)methyl)-5-(trifluoromethyl)benzamide (Compound No. 6)

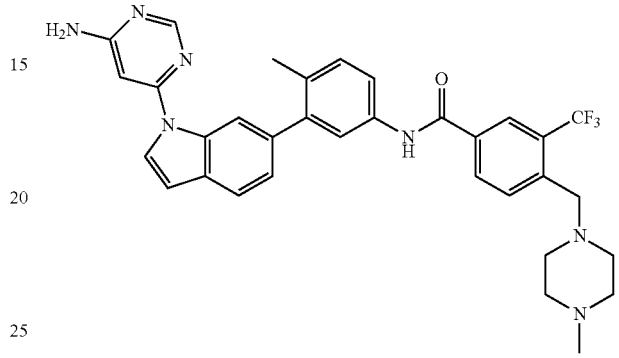

The target compound was obtained using the method described in Example 1 above and an appropriate starting material.

¹H NMR (400 MHz, MeOD-d₆) δ 8.32 (d, J=0.8 Hz, 1H), 8.28 (s, 1H), 8. 22 (s, 1H), 8.10 (dd, J=1.2 Hz, 8.0 Hz, 1H), 7.91 (d, J=8.0 Hz, 1H), 7.83 (d, J=3.6 Hz, 1H), 7.63-7.57 (m, 3H), 7.25 (d, J=8.0 Hz, 1H), 7.15 (dd, J=1.2 Hz, 8.0 Hz, 1H), 6.73 (d, J=3.6 Hz, 1H), 6.67 (d, J=1.2 Hz, 1H), 3.70 (s, 2H), 2.51 (bs, 8H), 2.29 (s, 3H), 2.25 (s, 3H), 2.14 (s, 3H)

Example 7

N-(3-(1-(6-aminopyrimidine-4-yl)-1H-indole-6-yl)phenyl)-3-(4-methyl-1H-imidazole-1-yl)-5-(trifluoromethyl)benzamide (Compound No. 7)

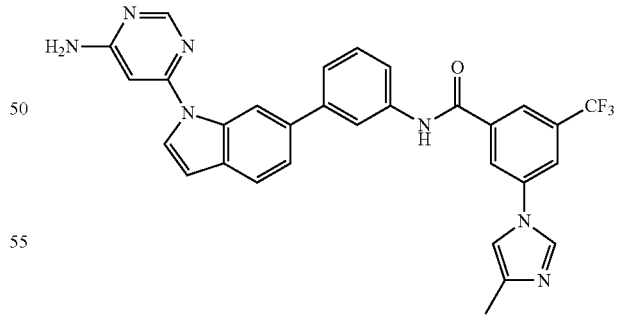

The target compound was obtained using the method described in Example 1 above and an appropriate starting material.

MS m/z [M+1] 555.07; ¹H NMR (400 MHz, DMSO-d₆) δ 10.62 (s, 1H), 8.61 (s, 1H), 8.49 (s, 1H), 8.42 (s, 2H), 8.26 (s, 1H), 8.21 (s, 1H), 8.01 (s, 1H), 7.95 (d, 1H), 7.85 (d, 1H), 7.76 (s, 1H), 7.73 (d, 1H), 7.54 (d, 1H), 7.50 (t, 1H), 7.47 (d, 1H), 7.06 (s, 2H), 6.80 (d, 1H), 6.68 (s, 1H), 2.19 (d, 3H).

Example 8

N-(3-(1-(6-aminopyrimidine-4-yl)-1H-indole-6-yl)phenyl)-3-morpholino-5-(trifluoromethyl)benzamide (Compound No. 8)

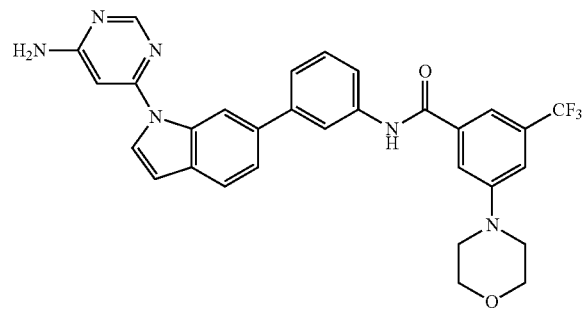 [SMILES: Nc1cc(-n2ccc3ccc(-c4cccc(NC(=O)c5cc(N6CCOCC6)cc(C(F)(F)F)c5)c4)cc32)ncn1]

The target compound was obtained using the method described in Example 1 above and an appropriate starting material.

MS m/z [M+1] 559.10; $^1$H NMR (400 MHz, DMSO-$d_6$) δ 10.46 (s, 1H), 8.60 (s, 1H), 8.47 (s, 1H), 8.04 (s, 1H), 7.95 (d, 1H), 7.88 (d, 1H), 7.75 (d, 1H), 7.73 (s, 1H), 7.69 (s, 1H), 7.51 (d, 1H), 7.49 (t, 1H), 7.47 (d, 1H), 7.40 (s, 1H), 7.06 (s, 2H), 6.80 (d, 1H), 6.68 (s, 1H), 3.77 (m, 4H), 3.37 (m, 4H).

Example 9

1-(3-(1-(6-aminopyrimidine-4-yl)-1H-indole-6-yl)-4-methylphenyl)-3-(2-methoxyphenyl) urea (Compound No. 9)

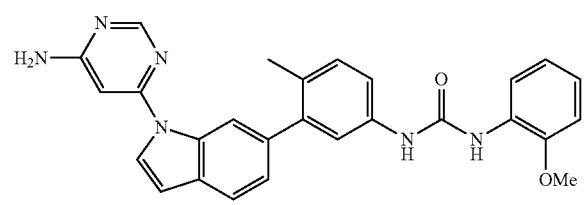 [SMILES: COc1ccccc1NC(=O)Nc1ccc(C)c(-c2ccc3ccn(-c4cc(N)ncn4)c3c2)c1]

6-(6-(5-amino-2-methylphenyl)-1H-indole-1-yl)pyrimidine-4-amine (30 mg, 0.25 mmol) obtained in step 4 of the Example 1 was dissolved in THF (1 mL). 1-isocyanato-2-methoxybenzene (32.6 µL, 0.25 mmol) was added at room temperature. The reaction solution was stirred at 50° C. for 3 hours and then cooled to room temperature. Ethyl acetate and water were added and the organic layers were separated. The aqueous solution layer was extracted with ethyl acetate and the collected organic layers were washed with brine, dried over magnesium sulfate and concentrated under reduced pressure. The residue was purified by column chromatography (silica gel, DCM:MeOH=20:1) to obtain 1-(3-(1-(6-aminopyrimidine-4-yl)-1H-indole-6-yl)-4-methylphenyl)-3-(2-methoxyphenyl)urea (74.3 mg, 0.16 mmol) as a white solid.

MS m/z [M+1] 465.00; $^1$H NMR (400 MHz, DMSO-$d_6$) δ 9.31 (s, 1H), 8.37 (s, 1H), 8.30 (s, 1H), 8.17 (s, 1H), 8.09 (d, 1H), 7.97 (d, 1H), 7.68 (d, 1H), 7.36 (s, 1H), 7.35 (d, 1H), 7.22 (d, 1H), 7.15 (d, 1H), 7.01 (s, 2H), 6.99 (d, 1H), 6.92 (t, 1H), 6.85 (t, 1H), 6.80 (d, 1H), 6.64 (s, 1H), 3.86 (s, 3H), 2.18 (s, 3H).

Example 10

1-(3-(1-(7H-pyrrolo[2,3-d]pyrimidine-4-yl)-1H-indole-6-yl)phenyl)-3-(2-methoxyphenyl)urea (Compound No. 10)

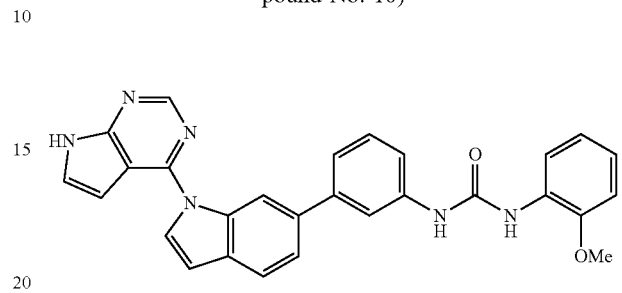

Step 1: (4-chloro-7H-pyrrolo[2,3-d]pyrimidine-7-yl)methyl pivalate

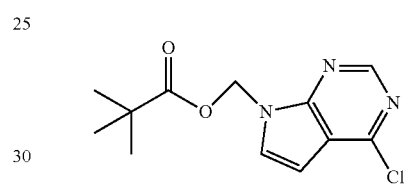

4-chloro-7H-pyrrolo[2,3-d]pyrimidine (100 mg, 0.651 mmol) was dissolved in tetrahydrofuran (5 mL). The temperature was lowered to 0° C., and sodium hydride (60% in mineral oil, 52 mg, 1.30 mmol) was added to the reaction solution. After 10 minutes, chloromethyl pivalate (0.19 mL, 1.30 mmol) was added at 0° C. After stirring for 1.5 hours at room temperature, the reaction solution was put into a saturated ammonium chloride aqueous solution. The organic layers were separated and the aqueous solution layer was extracted with ethyl acetate. The collected organic layers were washed with brine, dried over magnesium sulfate and concentrated under reduced pressure. The residue was purified by column chromatography (silica gel, EA:Hx=1:4) to obtain (4-chloro-7H-pyrrolo[2,3-d]pyrimidine-7-yl)methyl pivalate (170 mg, 0.635 mmol) as a white solid.

MS m/z [M+1] 268.01.

Step (4-(6-(3-nitrophenyl)-1H-indole-1-yl)-7H-pyrrolo[2,3-d]pyrimidine-7-yl)methyl pivalate

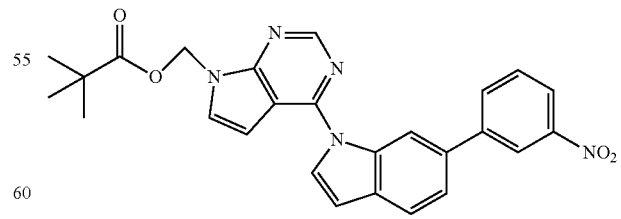

In an airtight container, 6-(3-nitrophenyl)-1H-indole (100 mg, 0.42 mmol) and (4-chloro-7H-pyrrolo[2,3-d]pyrimidine-7-yl)methyl pivalate (112 mg, 0.42 mmol) were dissolved in 1,4-dioxane (5 mL), and then Cs$_2$CO$_3$ (270 mg, 0.83 mmol) was added. After removing the gas of solution using ultrasonic waves, Xantphos (CAS No. 161265-03-8; 49 mg, 0.084 mmol) and Pd (OAc)$_2$ (9.4 mg, 0.042 mmol) were added continuously, and then the reaction solution was stirred at 120° C. for 2 hours. After cooling it to room temperature, ethyl acetate and water were added, and the water layers were extracted with ethyl acetate. The collected organic layers were washed with brine, dried over magnesium sulfate and concentrated under reduced pressure. The residue was purified by column chromatography (silica gel, 100% methylene chloride) to obtain (4-(6-(3-nitrophenyl)-1H-indole-1-yl)-7H-pyrrolo[2,3-d]pyrimidine-7-yl)methyl pivalate (177 mg, 0.377 mmol) as a white solid.

MS m/z [M+1] 470.03; $^1$H NMR (400 MHz, DMSO-d$_6$) δ 8.91 (s, 1H), 8.89 (s, 1H), 8.45 (s, 1H), 8.26 (d, J=3.53 Hz, 1H), 8.20 (d, J=8.23 Hz, 1H), 8.17 (d, J=7.30 Hz, 1H), 7.85 (d, J=7.65 Hz, 1H), 7.82 (d, J=3.62 Hz, 1H), 7.78 (t, J=7.97 Hz, 1H), 7.66 (dd, J=5.8, 6.71 Hz, 1H), 7.03 (d, J=3.79 Hz, 1H), 6.97 (d, J=3.50 Hz, 1H), 6.30 (s, 2H), 1.10 (s, 9H).

Step 3: (4-(6-(3-aminophenyl)-1H-indole-1-yl)-7H-pyrrolo[2,3-d]pyrimidine-7-yl)methyl pivalate

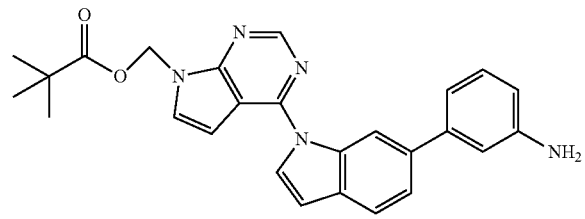 [SMILES: CC(C)(C)C(=O)OCn1ccc2c(-n3ccc4ccc(-c5cccc([N+](=O)[O-])c5)cc43)ncnc21]

(4-(6-(3-nitrophenyl)-1H-indole-1-yl)-7H-pyrrolo[2,3-d]pyrimidine-7-yl)methyl pivalate (166 mg, 0.35 mmol) was dissolved in ethanol (5 mL). Tin (II) chloride dihydrate (SnCl$_2$.2H$_2$O; 80 mg, 1.75 mmol) was added, and the reaction solution was stirred at 80° C. for 1.5 hours. After cooling it to room temperature, the reaction solution was basified to pH 8 with ammonia water, and then ethyl acetate and sodium carbonate were added. The mixture solution was filtered through a pad of diatomaceous earth and the filtrate was concentrated under reduced pressure. The residue was purified by column chromatography (silica gel, DCM:MeOH=20:1) to obtain (4-(6-(3-aminophenyl)-1H-indole-1-yl)-7H-pyrrolo[2,3-d]pyrimidine-7-yl)methyl pivalate (120 mg, 0.27 mmol) as a whitening solid.

MS m/z [M+1] 440.08; $^1$H NMR (400 MHz, DMSO-d$_6$) δ 8.89 (s, 1H), 8.76 (s, 1H), 8.18 (d, J=3.56 Hz, 1H), 7.81 (d, J=3.83 Hz, 1H), 7.72 (d, J=8.12 Hz, 1H), 7.44 (dd, J=1.54, 8.15 Hz), 7.10 (t, J=7.69 Hz, 1H), 7.02 (d, J=3.82 Hz, 1H), 6.92 (d, J=3.53 Hz, 1H), 6.88 (s, 1H), 6.80 (d, J=7.5 Hz, 1H), 6.54 (dd, J=2.08, 7.94 Hz, 1H), 6.29 (s, 2H), 5.16 (s, 2H), 1.10 (s, 9H).

Step 4: 1-(3-(1-(7H-pyrrolo[2,3-d]pyrimidine-4-yl)-1H-indole-6-yl)phenyl)-3-(2-methoxyphenyl)urea

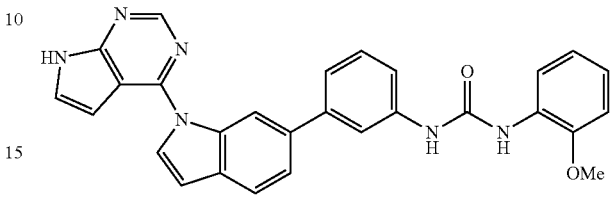

(4-(6-(3-aminophenyl)-1H-indole-1-yl)-7H-pyrrolo[2,3-d]pyrimidine-7-yl)methyl pivalate (30 mg, 0.068 mmol) was dissolved in THF (1 mL). 1-isocyanato-2-methoxybenzene (32.6 μL, 0.25 mmol) was added at room temperature. The reaction solution was stirred at 50° C. for 3 hours and then cooled to room temperature. 1 N NaOH (1 mL) and MeOH (1 mL) were added, and the mixture solution was stirred at room temperature for 2 hours. Ethyl acetate and water were added and the organic layers were separated. The aqueous solution layer was extracted with ethyl acetate and the collected organic layers were washed with brine, dried over magnesium sulfate and concentrated under reduced pressure. The residue was purified by column chromatography (silica gel, DCM:MeOH=20:1) to obtain 1-(3-(1-(7H-pyrrolo[2,3-d]pyrimidine-4-yl)-1H-indole-6-yl)phenyl)-3-(2-methoxyphenyl)urea (24.3 mg, 0.051 mmol) as a white solid.

MS m/z [M+1] 475.18; $^1$H NMR (400 MHz, DMSO-d$_6$) δ 9.46 (s, 1H), 8.81 (s, 1H), 8.78 (s, 1H), 8.25 (s, 1H), 8.21 (d, J=3.55 Hz, 1H), 8.15 (dd, J=1.62, 7.82 Hz, 1H), 7.79 (s, 1H), 7.77 (d, J=2.31 Hz, 1H), 7.67 (d, J=3.57 Hz, 1H), 7.49 (dd, J=1.34, 8.13 Hz, 1H), 7.44 (d, J=8.78 Hz, 1H), 7.38 (t, J=7.75 Hz, 1H), 7.27 (d, J=7.53 Hz, 1H), 7.01 (dd, J=1.35, 8.03 Hz, 1H), 6.95 (t, J=5.81 Hz, 1H), 6.92 (d, J=3.02 Hz, 1H), 6.91 (t, J=1.48 Hz, 1H), 6.89 (d, J=3.62 Hz, 1H), 3.88 (s, 3H).

Compound Nos. 11 to 16 were synthesized based on the following reaction formula 2.

[Reaction Formula 2]

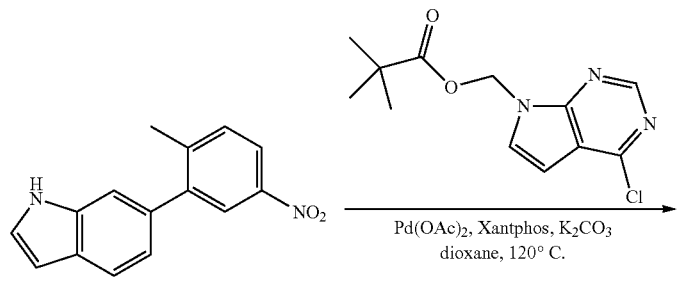

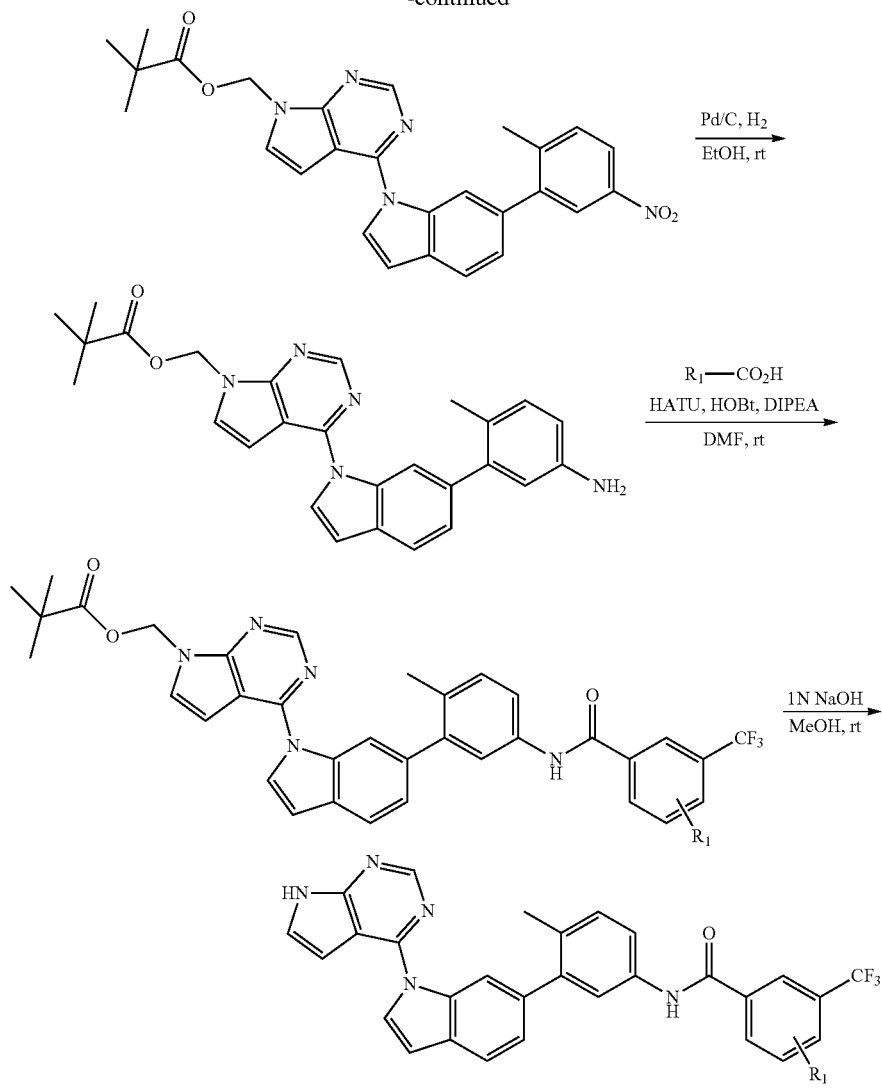

Example 11

N-(3-(1-(7H-pyrrolo[2,3-d]pyrimidine-4-yl)-1H-indole-6-yl)-4-methylphenyl)-3-(4-methyl-1H-imidazole-1-yl)-5-(trifluoromethyl)benzamide (Compound No. 11)

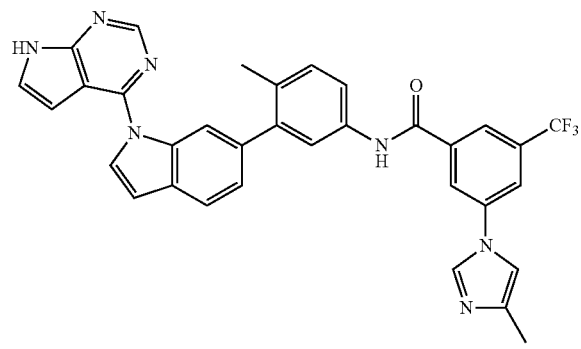 [SMILES: Cc1cn(-c2cc(C(=O)Nc3ccc(C)c(-c4ccc5ccn(-c6ncnc7[nH]ccc67)c5c4)c3)cc(C(F)(F)F)c2)cn1]

Step 1: (4-(6-(2-methyl-5-nitrophenyl)-1H-indole-1-yl)-7H-pyrrolo[2,3-d]pyrimidine-7-yl)methyl pivalate 6-(2-methyl-5-nitrophenyl)-1H-indole (1 g, 4.2 mmol) was dissolved in 1,4-dioxane solution (28 mL). (4-chloro-7H-pyrrolo[2,3-d]pyrimidine-7-yl)methyl pivalate (1.35 g, 5.04 mmol) and potassium carbonate (1.74 g, 12.6 mmol) were added, and then a nitrogen gas was injected for 5 minutes to remove the gas included in the mixture solution. Then, the reaction vessel was placed in an oil bath heated to 120° C., and Pd(OAc)$_2$ (95 mg, 0.42 mmol) and Xantphos (365 mg, 0.63 mmol) were added and stirred for 2 hours. After the reaction was completed, it was extracted with ethyl acetate and water. The collected organic layers were dried over anhydrous sodium sulfate and concentrated. The residue was purified by MPLC to obtain the target compound (3.53 g, 72%) as a yellow solid.

$^1$H NMR (400 MHz, CDCl$_3$-d$_6$) δ 8.84 (s, 1H), 8.56 (s, 1H), 8.20 (d, J=2.4 Hz, 1H), 8.11 (dd, J=2.4 Hz, 8.4 Hz, 1H), 7.95 (d, J=3.6 Hz, 1H), 7.73 (d, J=8.0 Hz, 1H), 7.51 (d, J=4.0 Hz, 1H), 7.43 (d, J=8.4 Hz, 1H), 7.21 (dd, J=1.6 Hz, 8.0 Hz, 1H), 6.87 (d, J=3.6 Hz, 1H), 6.79 (d, J=4.0 Hz, 1H), 6.28 (s, 2H), 2.42 (s, 3H), 1.17 (s, 9H)

Step 2: (4-(6-(5-amino-2-methylphenyl)-1H-indole-1-yl)-7H-pyrrolo[2,3-d]pyrimidine-7-yl)methyl pivalate 4-(6-(2-methyl-5-nitrophenyl)-1H-indole-1-yl)-7H-pyrrolo[2,3-d]pyrimidine-7-yl)methyl pivalate (1 g, 2.07 mmol) was dissolved in the mixture solution of ethyl acetate/ethanol (1:1, 50 mL), Pd/C (100 mg) was slowly added and stirred for 12 hours while injecting hydrogen gas. After the reaction was completed, it was filtered using a celite pad, and the residue was concentrated and directly used in the subsequent reaction without further purification.

Step 3: N-(3-(1-(7H-pyrrolo[2,3-d]pyrimidine-4-yl)-1H-indole-6-yl)4-methylphenyl)-3-(4-methyl-1H-imidazole-1-yl)-5-(trifluoromethyl)benzamide (4-(6-(5-amino-2-methylphenyl)-1H-indole-1-yl)-7H-pyrrolo[2,3-d]pyrimidine-7-yl)methyl pivalate and 3-(4-methyl-1H-imidazole-1-yl)-5-(trifluoromethyl)benzoic acid were used to synthesize a compound having an amide bond by performing the same methods as step 5 of the Example 1. Then, 1 N NaOH aqueous solution was added, followed by stirring for 1 hour, and was extracted by using ethyl acetate and water. The collected organic layers were dried over anhydrous sodium sulfate and concentrated. The residue was purified by MPLC to obtain the target compound as a white solid.

$^1$H NMR (400 MHz, DMSO-d$_6$) δ 12.43 (bs, 1H), 10.48 (s, 1H), 8.71 (s, 1H), 8.58 (t, J=0.8 Hz, 1H), 8.44 (s, 1H), 8.38 (d, J=1.2 Hz, 1H), 8.22 (d, J=3.6 Hz, 1H), 8.22 (s, 1H), 8.16 (s, 1H), 7.76 (dd, J=2.0 Hz, 8.0 Hz, 1H), 7.76 (d, J=8.0 Hz, 1H), 7.69-7.65 (m, 3H), 7.33 (d, J=8.4 Hz, 1H), 7.24 (dd, J=1.2 Hz, 8.0 Hz, 1H), 6.94 (dd, J=0.4 Hz, 3.6 Hz, 1H), 6.90 (d, J=3.6 Hz, 1H), 2.25 (s, 3H), 2.17 (d, J=0.8 Hz, 3H)

Example 12

N-(3-(1-(7H-pyrrolo[2,3-d]pyrimidine-4-yl)-1H-indole-6-yl)-4-methylphenyl)-3-(4-hydroxypiperidine-1-yl)-5-(trifluoromethyl)benzamide (Compound No. 12)

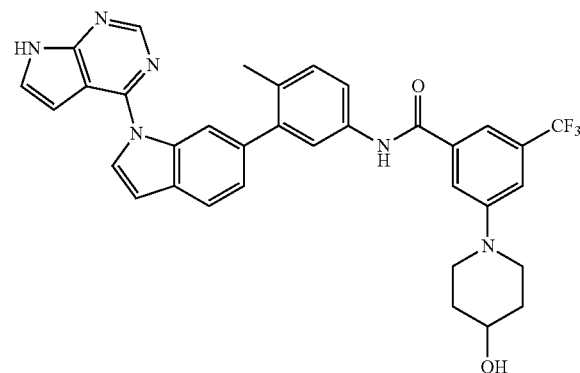 [SMILES: Cc1ccc(NC(=O)c2cc(N3CCC(O)CC3)cc(C(F)(F)F)c2)cc1-c1ccc2ccn(-c3ncnc4[nH]ccc34)c2c1]

The target compound was obtained using the method described in Example 11 above and an appropriate starting material.

$^1$H NMR (400 MHz, DMSO-d$_6$) δ 12.42 (bs, 1H), 10.31 (s, 1H), 8.71 (s, 1H), 8.57 (s, 1H), 8.22 (d, J=3.6 Hz, 1H), 7.75 (d, J=8.0 Hz, 1H), 7.74 (d, J=8.0 Hz, 1H), 7.69 (s, 1H), 7.66-7.65 (m, 2H), 7.56 (s, 1H), 7.32 (d, J=8.4 Hz, 1H), 7.23 (dd, J=1.2 Hz, 8.0 Hz, 1H), 6.91 (dd, J=3.6 Hz, 9.6 Hz, 2H), 4.71 (d, J=4.4 Hz, 1H), 3.70-3.66 (m, 3H), 3.04-2.98 (m, 2H), 2.24 (s, 3H), 1.83-1.81 (m, 2H), 1.50-1.41 (m, 2H)

Example 13

N-(3-(1-(7H-pyrrolo[2,3-d]pyrimidine-4-yl)-1H-indole-6-yl)-4-methylphenyl)-3-morpholino-5-(trifluoromethyl)benzamide (Compound No. 13)

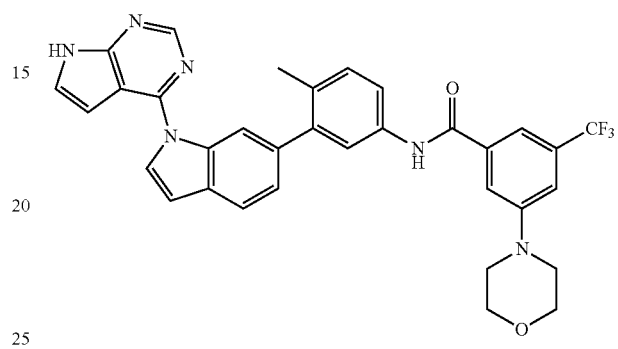

The target compound was obtained using the method described in Example 11 above and an appropriate starting material.

$^1$H NMR (400 MHz, DMSO-d$_6$) δ 12.42 (bs, 1H), 10.32 (s, 1H), 8.70 (s, 1H), 8.56 (s, 1H), 8.22 (d, J=3.6 Hz, 1H), 7.75 (d, J=7.6 Hz, 1H), 7.74 (dd, J=2.0 Hz, 8.4 Hz, 1H), 7.70 (s, 1H), 7.66-7.64 (m, 3H), 7.36 (s, 1H), 7.30 (d, J=8.4 Hz, 1H), 7.22 (dd, J=1.6 Hz, 8.4 Hz, 1H), 6.93 (d, J=3.6 Hz, 1H), 6.90 (d, J=4.0 Hz, 1H), 3.76-3.73 (m, 4H), 3.28-3.26 (m, 4H), 2.24 (s, 3H)

Example 14

N-(3-(1-(7H-pyrrolo[2,3-d]pyrimidine-4-yl)-1H-indole-6-yl)-4-methylphenyl)-3-(4-methylpiperazine-1-yl)-5-(trifluoromethyl)benzamide (Compound No. 14)

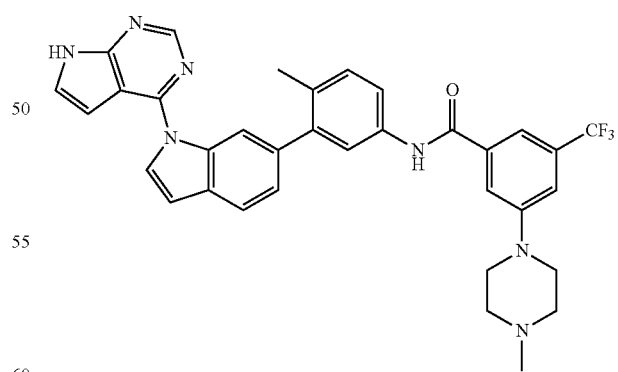

The target compound was obtained using the method described in Example 11 above and an appropriate starting material.

$^1$H NMR (400 MHz, Acetone-d$_6$) δ 11.51 (bs, 1H), 9.74 (bs, 1H), 8.69 (s, 1H), 8.65 (s, 1H), 8.18 (d, J=3.2 Hz, 1H), 7.79 (dd, J=2.4 Hz, 8.4 Hz, 1H), 7.76 (s, 1H), 7.73 (d, J=10.0

Hz, 1H), 7.72 (s, 1H), 7.64-7.62 (m, 2H), 7.34 (s, 1H), 7.29 (d, J=8.0 Hz, 1H), 7.24 (dd, J=1.6 Hz, 8.0 Hz, 1H), 6.93-6.90 (m, 2H), 3.35-3.33 (m, 4H), 2.28 (s, 3H), 2.25 (s, 3H)

Example 15

N-(3-(1-(7H-pyrrolo[2,3-d]pyrimidine-4-yl)-1H-indole-6-yl)-4-methylphenyl)-4-(4-methylpiperazine-1-yl)-5-(trifluoromethyl)benzamide (Compound No. 15)

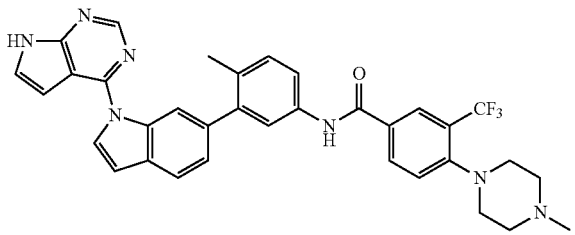 [SMILES: Cc1ccc(NC(=O)c2ccc(N3CCN(C)CC3)c(C(F)(F)F)c2)cc1-c1ccc2ccn(-c3ncnc4[nH]ccc34)c2c1]

The target compound was obtained using the method described in Example 11 above and an appropriate starting material.

$^1$H NMR (400 MHz, Acetone-d$_6$) δ 11.63 (bs, 1H), 9.75 (bs, 1H), 8.70 (s, 1H), 8.66 (s, 1H), 8.27 (d, J=1.6 Hz, 1H), 8.21 (dd, J=2.0 Hz, 8.4 Hz, 1H), 8.15 (d, J=3.6 Hz, 1H), 7.79 (dd, J=2.0 Hz, 8.0 Hz, 1H), 7.78 (d, J=2.0 Hz, 1H), 7.71 (d, J=8.0 Hz, 1H), 7.60 (d, J=7.6 Hz, 1H), 7.50 (d, J=8.8 Hz, 1H), 7.26 (d, J=8.4 Hz, 1H), 7.23 (dd, J=1.6 Hz, 8.0 Hz, 1H), 6.89 (t, J=4.0 Hz, 2H), 2.99-2.96 (m, 4H), 2.49 (bs, 4H), 2.28 (s, 3H), 2.25 (s, 3H)

Example 16

N-(3-(1-(7H-pyrrolo[2,3-d]pyrimidine-4-yl)-1H-indole-6-yl)-4-methylphenyl)-4-((4-methylpiperazine-1-yl)methyl)-3-(trifluoromethyl)benzamide (Compound No. 16).

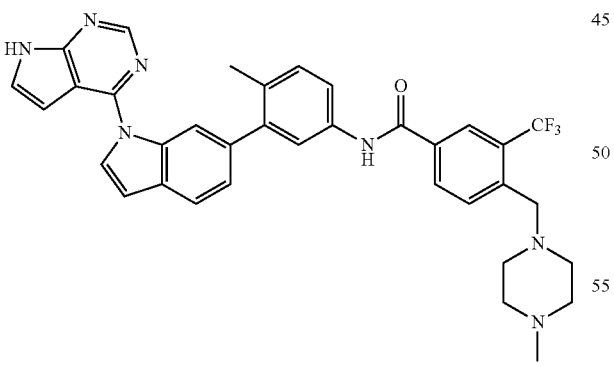

The target compound was obtained using the method described in Example 11 above and an appropriate starting material.

$^1$H NMR (400 MHz, Acetone-d$_6$) δ 11.62 (bs, 1H), 9.81 (s, 1H), 8.70 (s, 1H), 8.68 (d, J=11.6 Hz, 1H), 8.27 (s, 1H), 8.22 (d, J=8.4 Hz, 1H), 8.16 (d, J=3.6 Hz, 1H), 7.94 (d, J=8.4 Hz, 1H), 7.81 (dd, J=2.4 Hz, 8.0 Hz, 1H), 7.76 (s, 1H), 7.72 (d, J=8.0 Hz, 1H), 7.61 (d, J=3.6 Hz, 1H), 7.28 (d, J=8.0 Hz, 1H), 7.24 (dd, J=1.2 Hz, 8.0 Hz, 1H), 6.90 (t, J=7.6 Hz, 2H), 3.67 (s, 2H), 2.46 (bs, 4H), 2.37 (bs, 4H), 2.29 (s, 3H), 2.17 (s, 3H)

Meanwhile, the novel compounds represented by the formula 1 according to the present invention can be prepared into various forms according to the purpose. The following is a description of some preparations containing the compound represented by the formula 1 as an active ingredient according to the present invention, but the present invention is not limited thereto.

Preparation Example

Preparation Example 1

Tablet (Direct Pressurization)

After 5.0 mg of the active ingredient was sieved, 14.1 mg of lactose, 0.8 mg of crospovidone USNF and 0.1 mg of magnesium stearate were mixed and pressurized to make tablets.

Preparation Example 2

Tablet (Wet Assembly)

After 5.0 mg of the active ingredient was sieved, 16.0 mg of lactose and 4.0 mg of starch were mixed. 0.3 mg of Polysorbate 80 was dissolved in the pure water, and an appropriate amount of this solution was added, followed by atomization. After drying, the granules were sieved and mixed with 2.7 mg of colloidal silicon dioxide and 2.0 mg of magnesium stearate. The granules were pressurized to make tablets.

Preparation Example 3

Powder and Capsules 5.0 mg of the active ingredient was sieved and mixed with 14.8 mg of lactose, 10.0 mg of polyvinyl pyrrolidone and 0.2 mg of magnesium stearate. The mixture was filled in a hard No. 5 gelatin capsules by using an appropriate device.

Preparation Example 4

Injections 100 mg was included as an active ingredient, and in addition, 180 mg of mannitol, 26 mg of Na$_2$HPO$_4$.12H$_2$O and 2974 mg of distilled water were added to prepare an injection.

Test Examples

Test Example 1

Proliferation Inhibitory Activity

The GI$_{50}$ value was calculated by measuring the inhibitory effect on the proliferation of the compounds of the present invention in parental Ba/F3, wt-Bcr-Abl Ba/F3, T315I-Bcr-Abl Ba/F3 and VEGFR2 Ba/F3 cell lines. The calculated GI$_{50}$ values are listed in the following Table 1.

TABLE 1

| Experimental compounds | Parental Ba/F3 | wt-Bcr-Abl Ba/F3 | T315I-Bcr-Abl Ba/F3 | VEGFR2 Ba/F3 |
|---|---|---|---|---|
| Compound No. 1 | B | B | A | C |
| Compound No. 2 | C | C | A | C |
| Compound No. 3 | C | C | A | C |
| Compound No. 4 | B | B | A | C |
| Compound No. 5 | B | B | A | C |
| Compound No. 6 | B | B | A | C |
| Compound No. 7 | C | C | B | C |
| Compound No. 8 | C | C | C | C |
| Compound No. 9 | C | C | C | C |
| Compound No. 10 | C | C | C | C |
| Compound No. 11 | B | A | A | C |
| Compound No. 12 | C | C | B | C |
| Compound No. 13 | C | B | B | C |
| Compound No. 14 | B | B | A | B |
| Compound No. 15 | B | B | A | B |
| Compound No. 16 | B | A | A | B |
| Ponatinib | B | A | A | A |

[Classification of GI$_{50}$]
A: less than 0.3 µM,
B: 0.3 to 3.0 µM,
C: 3.0 µM or more According to the results listed in the above Table 1, Ponatinib drug strongly inhibits wild-type Bcr-Abl and T315I-Bcr-Abl and has a strong inhibitory activity against VEGFR2 kinase, thereby causing side-effects such as the inhibition of bone marrow production, pancreatitis, and cardiovascular disease.

However, the compounds of the present invention have activity to inhibit wt-Bcr-Abl and T315I-Bcr-Abl, and the inhibitory activity against VEGFR2 kinase is weak, so that it can be understood that no adverse drug effect is induced. In particular, the compounds of Compound Nos. 1, 4, 5, 6 and 11 have a wt-Bcr-Abl inhibitory activity, and thus are useful as a target drug of CML and have strong inhibitory activity against the mutant species T315I-Bcr-Abl. Therefore, it is useful as a CML drug having no drug-resistance and side-effects because there is no fear of side-effects of drugs because it has excellent drug-resistance, and at the same time, it does not exhibit any inhibitory activity against VEGFR2 kinase.

Test Example 2

Animal Efficacy Test

In order to confirm that the compounds of the present invention are useful as a pharmaceutical composition for the treatment, prevention and alleviation of chronic myelogenous leukemia with reduced side-effects in comparison to the Ponatinib control drug, the following animal efficacy tests were conducted.

Female BalB/C nude mice (Nara-Biotech, South Korea) of 5 to 6 weeks of age were used as experimental animals. Ba/F3 cells simultaneously expressing T315I BCR-Abl mutation and luciferase were intravenously injected through the tail vein of the experimental animal at a dose of 1×10⁶. The experimental compounds (n=8, Imatinib 60 mpk, Ponatinib 30 mpk, compound 30 mpk of Compound No. 1 and excipient control group) were orally administered once daily at the same time for 8 days from the 4$^{th}$ day from the injection.

FIG. 1 attaches a photograph of measuring the bioluminescence obtained by using the IVIS-200 in vivo imaging system (PerkinElmer, USA) on the 1$^{st}$, 5$^{th}$ and 9$^{th}$ days from the oral administration of each of the excipient control group, Imatinib, Ponatinib or a compound of Compound No. 1.

Figure 2:
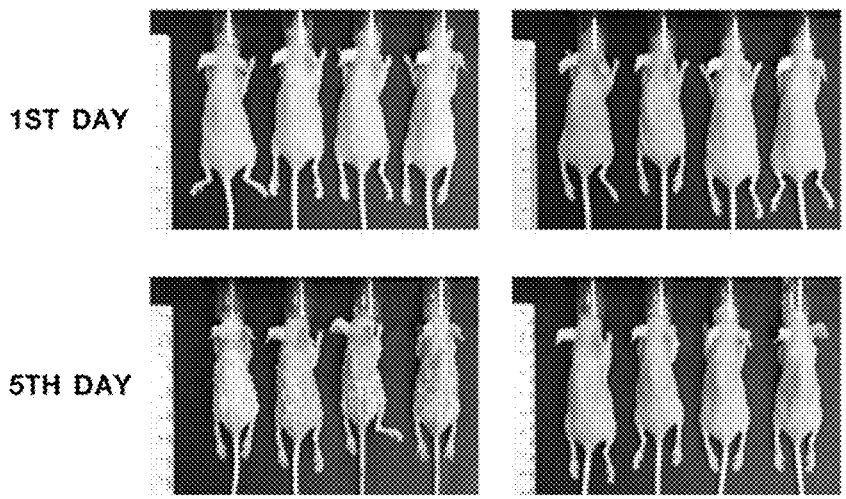
FIG. 2 is a photograph comparing the degree of occurrence of side-effects on the $1^{st}$ day and the $5^{th}$ day after the oral administration of Ponatinib or a compound of Compound No. 1.
Figure 3:
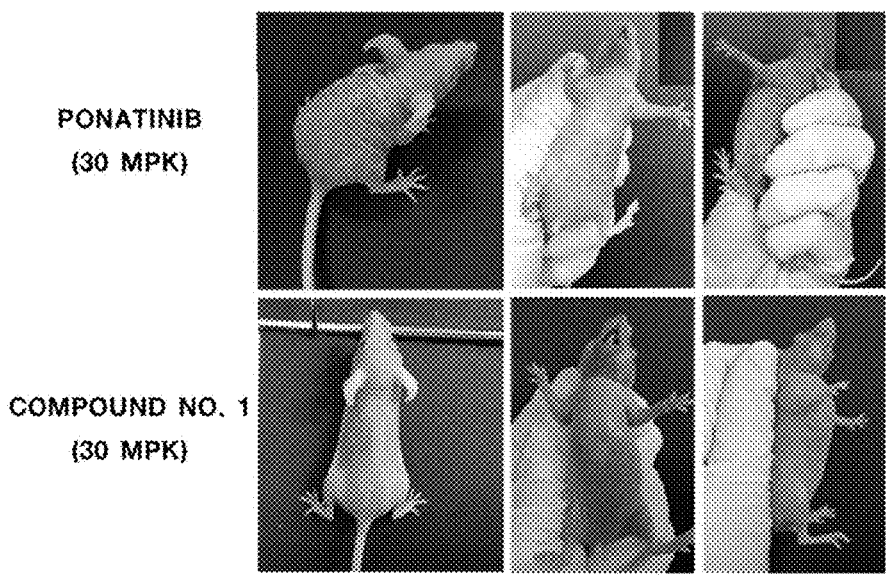
FIG. 3 is an enlarged photograph comparing the degree of occurrence of side-effects on the $5^{th}$ day after the oral administration of Ponatinib or a compound of Compound No. 1.

FIGS. 2 and 3 attach photographs showing a visual comparison of the degree of occurrence of side-effects of the experimental animals to which Ponatinib or a compound of Compound No. 1 was orally administered. FIG. 2 is a photograph comparing the degree of occurrence of side-effects on the 1$^{st}$ and 5$^{th}$ days from the oral administration. FIG. 3 is an enlarged photograph comparing the degree of occurrence of side-effects on the 5$^{th}$ day from the oral administration.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A pharmaceutical composition for the treatment and alleviation of chronic myelogenous leukemia with reduced drug-resistance and drug side-effects, comprising 1,6-disubstituted indole compounds selected from the group consisting of:

N-(3-(1-(6-aminopyridine-4-yl)-1H-indole-6-yl)-4-methylphenyl)-3-(4-methyl-1H-imidazole-1-yl)-5-(trifluoromethyl)benzamide (Compound No. 1);

N-(3-(1-(6-aminopyridine-4-yl)-1H-indole-6-yl)-4-methylphenyl)-3-(4-hydroxypiperidine-1-yl)-5-(trifluoromethyl)benzamide (Compound No. 2);

N-(3-(1-(6-aminopyridine-4-yl)-1H-indole-6-yl)-4-methylphenyl)-3-morpholino-5-(trifluoromethyl)benzamide (Compound No. 3);

N-(3-(1-(6-aminopyridine-4-yl)-1H-indole-6-yl)-4-methylphenyl)-3-(4-methylpiperazine-1-yl)-5-(trifluoromethyl)benzamide (Compound No. 4);

N-(3-(1-(6-aminopyridine-4-yl)-1H-indole-6-yl)-4-methylphenyl)-4-(4-methylpiperazine-1-yl)-5-(trifluoromethyl)benzamide (Compound No. 5);

N-(3-(1-(6-aminopyridine-4-yl)-1H-indole-6-yl)-4-methylphenyl)-3-((4-methylpiperazine-1-yl)methyl)-5-(trifluoromethyl)benzamide (Compound No. 6);

N-(3-(1-(7H-pyrrolo[2,3-d]pyrimidine-4-yl)-1H-indole-6-yl)-4-methylphenyl)-3-(4-methyl-1H)-imidazole-1-yl)-5-(trifluoromethyl)benzamide (Compound No. 11);

N-(3-(1-(7H-pyrrolo[2,3-d]pyrimidine-4-yl)-1H-indole-6-yl)-4-methylphenyl)-3-(4-hydroxypiperidine-1-yl)-5-(trifluoromethyl)benzamide (Compound No. 12);

N-(3-(1-(7H-pyrrolo[2,3-d]pyrimidine-4-yl)-1H-indole-6-yl)-4-methylphenyl)-3-morpholino-5-(trifluoromethyl)benzamide (Compound No. 13);

N-(3-(1-(7H-pyrrolo[2,3-d]pyrimidine-4-yl)-1H-indole-6-yl)-4-methylphenyl)-3-(4-methylpiperazine-1-yl)-5-(trifluoromethyl)benzamide (Compound No. 14);

N-(3-(1-(7H-pyrrolo[2,3-d]pyrimidine-4-yl)-1H-indole-6-yl)-4-methylphenyl)-4-(4-methylpiperazine-1-yl)-5-(trifluoromethyl)benzamide (Compound No. 15); and N-(3-(1-(7-pyrrolo[2,3-d]pyrimidine-4-yl)-1H-indole-6-yl)-4-methylphenyl)-4-((4-methylpiperazine-1-yl)methyl)-3-(trifluoromethyl)benzamide (Compound No. 16), or a pharmaceutically acceptable salt thereof, as an active ingredient.

2. The pharmaceutical composition of claim 1, comprising a compound selected from the group consisting of:

N-(3-(1-(6-aminopyridine-4-yl)-1H-indole-6-yl)-4-methylphenyl)-3-(4-methyl-1H-imidazole-1-yl)-5-(trifluoromethyl)benzamide (Compound No. 1);

N-(3-(1-(6-aminopyridine-4-yl)-1H-indole-6-yl)-4-methylphenyl)-3-(4-hydroxypiperidine-1-yl)-5-(trifluoromethyl)benzamide (Compound No. 2);

N-(3-(1-(6-aminopyridine-4-yl)-1H-indole-6-yl)-4-methylphenyl)-3-morpholino-5-(trifluoromethyl)benzamide (Compound No. 3);

N-(3-(1-(6-aminopyridine-4-yl)-1H-indole-6-yl)-4-methylphenyl)-3-(4-methylpiperazine-1-yl)-5-(trifluoromethyl)benzamide (Compound No. 4);

N-(3-(1-(6-aminopyridine-4-yl)-1H-indole-6-yl)-4-methylphenyl)-4-(4-methylpiperazine-1-yl)-5-(trifluoromethyl)benzamide (Compound No. 5);

N-(3-(1-(6-aminopyridine-4-yl)-1H-indole-6-yl)-4-methylphenyl)-3-((4-methylpiperazine-1-yl)methyl)-5-(trifluoromethyl)benzamide (Compound No. 6);

N-(3-(1-(7H-pyrrolo[2,3-d]pyrimidine-4-yl)-1H-indole-6-yl)-4-methylphenyl)-3-(4-methylpiperazine-1-yl)-5-(trifluoromethyl)benzamide (Compound No. 14);

N-(3-(1-(7H-pyrrolo[2,3-d]pyrimidine-4-yl)-1H-indole-6-yl)-4-methylphenyl)-4-(4-methylpiperazine-1-yl)-5-(trifluoromethyl)benzamide (Compound No. 15); and N-(3-(1-(7H-pyrrolo[2,3-d]pyrimidine-4-yl)-1H-indole-6-yl)-4-methylphenyl)-4-((4-methylpiperazine-1-yl)methyl)-3-(trifluoromethyl)benzamide (Compound No. 16), or a pharmaceutically acceptable salt thereof as an active ingredient.

3. The pharmaceutical composition of claim 1, wherein the side-effects are inhibition of bone marrow production, pancreatitis induction, or cardiovascular disease.

4. The pharmaceutical composition of claim 1, exhibiting a proliferation inhibitory activity against a Bcr-Abl fusion protein, which is a causative gene of chronic myelogenous leukemia (CML), exhibiting an inhibitory activity against T315I-Bcr-Abl gatekeeper mutant species, and exhibiting no inhibitory activity against VEGFR2 protein kinase.

* * * * *